US007850648B2

(12) United States Patent
Gratwohl et al.

(10) Patent No.: US 7,850,648 B2
(45) Date of Patent: Dec. 14, 2010

(54) NEEDLE PROTECTING DEVICE COMPRISING A LOCK

(75) Inventors: Christian Gratwohl, Aarau (CH); Martin Wymann, Liebefeld (CH)

(73) Assignee: TecPharma Licensing AG, Burgdorf (CH)

( * ) Notice: Subject to any disclaimer, the term of this patent is extended or adjusted under 35 U.S.C. 154(b) by 23 days.

(21) Appl. No.: 11/850,387

(22) Filed: Sep. 5, 2007

(65) Prior Publication Data
US 2008/0077093 A1 Mar. 27, 2008

(30) Foreign Application Priority Data
Sep. 6, 2006 (DE) ............. 10 2006 041 809

(51) Int. Cl.
*A61M 5/00* (2006.01)
(52) U.S. Cl. .............. 604/110; 604/164.08; 604/192; 604/197; 604/198
(58) Field of Classification Search .......... 604/110, 604/192–198, 181, 187, 164.08
See application file for complete search history.

(56) References Cited
U.S. PATENT DOCUMENTS
4,929,241 A * 5/1990 Kulli ............... 604/263
5,088,988 A * 2/1992 Talonn et al. ......... 604/198
6,773,415 B2 * 8/2004 Heiniger ............ 604/110

FOREIGN PATENT DOCUMENTS
DE 10203597 A1 8/2003
DE 202004016791 U1 12/2005
EP 1267966 B1 1/2003

* cited by examiner

Primary Examiner—Kevin C Sirmons
Assistant Examiner—Larry R Wilson
(74) Attorney, Agent, or Firm—Dorsey & Whitney LLP; David E. Bruhn, Esq.

(57) ABSTRACT

A needle unit for an injection device comprising an injection needle and a needle holder, the needle unit coupled to the injection device and comprising: a needle protector comprising a guide which guides the needle protector such that it can move axially, at least one spring element applying a spring force to the needle protector thus holding the protector in a first position, and a lock which, after an injection, locks the needle protector in the first position against moving further axially, wherein the lock is deformable by force and assumes its original shape after said force is removed, and wherein the needle protector affects the lock transversely with respect to the axial movement direction during an axial movement of the protector which accompanies an injection and deflects the lock into a locking position when the needle protector is moved to the first position.

11 Claims, 5 Drawing Sheets

NEEDLE PROTECTING DEVICE COMPRISING A LOCK

CROSS-REFERENCE TO RELATED APPLICATIONS

This application claims benefit of priority to German Application No. DE 102006 041 809.3 filed on Sep. 6, 2006, the content of which is incorporated in its entirety herein by reference.

BACKGROUND

The present invention relates to devices for injecting, infusing, administering, delivering and dispensing substances, and to methods for making and using such devices, as well as to related peripheral, adjunct, complementary, cooperative and auxiliary devices and methods. More particularly, the present invention relates to a needle unit for a syringe or injection device, such as a "pen" for self-medication by the patient, and to injection devices comprising such a needle unit.

Needle units, which in their delivered state surround an injection needle to protect a user from injury and which, once used, latch in a secure position in which they again surround the injection needle over its entire length, are known in the prior art. Typically, the needle surrounding structure can only be moved out of its latched state by force, which then results in the destruction of the needle unit. This secure connection after use is intended to protect against injury to the user after injecting, injury of the disposal staff when disposing of the needle units, and to provide that the needle unit is used properly and only once, so as to ensure the sterility of the needle unit when it is used.

EP 1 267 966 B1 discloses an injector cap for an ampoule support, said cap comprising a sliding sleeve which is mounted such that it can shift on it, wherein the sliding sleeve is pressed by a biasing means into a first, front position in which it hides a cannula. The sliding sleeve can be shifted, against the bias, into a second position in which the cannula emerges from the front facing end. A locking device is provided in the sliding sleeve which is slaved by the sliding sleeve on its way to the second position. Once the injection is complete, the biasing means presses the sliding sleeve back into its initial position in which it securely surrounds the cannula. The locking device is not slaved in this return movement, but rather latches on the cannula support. When the sliding sleeve is in its final position, the locking device establishes a secure connection via a locking means, which locks the sliding sleeve against shifting further.

One disadvantage of this injector cap is that the locking device has to be connected to the cannula support first, before it can lock the sliding sleeve against shifting further. This, however, also means that if the user does not slide the sliding sleeve back far enough, for example by employing too little force, the connection between the cannula support and the sliding sleeve is not established, hence the locking means is pressed back into the initial position again together with the sliding sleeve and the injector cap can thus continue to be used.

SUMMARY

It is an object of the invention to provide a needle covering or protecting device which is simple to manufacture and securely protects the user from contact with the injection needle after an injection. It is another object of the invention to provide a reliable and secure lock for the needle covering or protecting device which makes it impossible to use the needle unit again.

In one embodiment, the present invention comprises a needle unit for an injection device comprising an injection needle and a needle holder, the needle unit coupled to the injection device and comprising: a needle protector (which also may be thought of and/or referred to as a cover or needle cover) comprising a guide which guides the needle protector such that it can move axially, at least one spring element applying a spring force to the needle protector thus holding the protector in a first position, and a lock which, after an injection, locks the needle protector in the first position against moving further axially, wherein the lock is deformable by force and assumes its original shape after said force is removed, and wherein the needle protector affects the lock transversely with respect to the axial movement direction during an axial movement of the protector which accompanies an injection and deflects the lock into a locking position when the needle protector is moved to the first position.

In one embodiment, the present invention comprises a needle unit for an injection device, the needle unit comprising an injection needle for injecting into a human or animal tissue, a needle holder, a needle protector comprising a guiding part which carries the needle protector such that it can move axially, at least one spring element which applies a spring force to the needle protector and thus holds the needle protector in a distal position, and at least one lock which, after an injection, locks the needle protector in the distal position against moving further axially, wherein the lock is dimensionally elastic and can be deformed by a force and assumes its original shape again once the force is removed, wherein the needle protector tenses the at least one lock in a direction transverse to the axial direction during an axial movement which accompanies an injection, and the at least one lock spring-deflects into a locking position when the needle protector is moved to the distal position.

The present invention relates to a needle protecting device which is fastened to an injection apparatus or ampoule or may be so fastened, and which comprises a needle holder for the fastening and an injection needle which protrudes in a distal direction. As used herein, "distal" means directed towards the surface of the patient's skin or pointing in the direction of the surface of the skin (thus generally referring to the forward or front end of a needle and the forward, front or needle-carrying end of an injection device); accordingly, "proximal" means pointing away from the surface of the skin (thus generally referring to the rear, rearward or back end of a needle or the rear, rearward or back end of an injection device).

In one embodiment, the present invention comprises a needle unit comprising an axially movable needle protection, wherein the needle protection securely envelops an injection needle before and after the needle unit is used and, after use, latches in a secure protective position such that it is no longer possible for the needle protection to move further in the axial direction, and/or such that attempting to so move the needle protection would result in the destruction of the needle unit. (The "axial direction" is the direction in which the longitudinal axis of the injection needle extends.) Such a needle unit is known from EP 1 267 966 B1, belonging to the owner of the present application, the disclosure of which is incorporated herein by reference.

The needle protecting device comprises a needle protector comprising a guiding part and a lock (which also may be thought of and/or referred to a locking system, block, locking mechanism, blocking mechanism, blocking means and like terms). In a preferred embodiment of the present invention, the guiding part is shaped substantially as a cylindrical body which is formed at its proximal end to be connected to a needle holder. The guiding part is fixedly—i.e. non-removably—connected, such as for example glued and fused, to the needle holder. However, it can also be detachably screwed or plugged onto the needle holder, as long as the guiding part cannot be moved in either the distal or proximal direction when it is present on the needle holder. The guiding part has a similar diameter to the needle holder, and may have almost the same diameter as the needle holder, i.e., the rotational axes of the two parts are substantially identical. It is, however, also possible for the guiding part to exhibit a different shape or a diameter which is greater or smaller or substantially deviates from the diameter of the needle holder, wherein the two rotational axes can in this case be offset parallel to each other. The parts can be suitable coupled as long as there is a secure connection between them.

The needle protection has the function of securely preventing injury to a patient or medical staff from or by the protruding and uncovered injection needle, before and after the medicine is dispensed. This can, for example, be facilitated by rod-shaped elements which protrude beyond the tip of the injection needle, wherein two such elements may be sufficient, depending on the local arrangement of the rod-shaped elements. Other options are, for example, a spiral, half-shell elements which can contact each other or are spaced from each other, a triangular, rectangular or polygonal protective covering or, in one preferred embodiment, a cylindrical cover. In principle, any shape or configuration of the needle protection or cover is conceivable as long as it provides that the user is protected from unintentional contact with the tip of the injection needle.

In some preferred embodiments, the needle protection comprises a needle protecting cover, a substantially cylindrical body or a body whose circumferential shape is similar or identical to the circumferential shape of the guiding part. It is open at its proximal end or comprises an opening, e.g., a central opening, for the injection needle at its distal end. An elastic element, for example a spring or a sliding part charged by a spring force, biases the needle protecting device in the distal direction, i.e. the needle protection is held in a secure position or guided back into a secure position by the elastic element before and after the medicine is dispensed. In this respect, "secure position" generally means a position in which the needle protection generally surrounds the injection needle over its entire length, such that injury to the user of the injection device by the tip of the injection needle is prevented. The needle protection can be shifted in the proximal direction, against the force of the elastic element, thus exposing the injection needle to dispense the medicine.

In one embodiment, the needle protecting device comprises a lock positioned on the needle holder. The lock can be fastened on the holder or molded onto or into it, and at least partially radially surrounds the holder and the injection needle or is arranged radially about it, wherein the term "radially" refers to the distal-proximal axis. The lock can be embodied in one or more parts. In some preferred embodiment, it comprises coupling elements or switching elements which can co-operate with coupling counter elements or switching counter elements of, for example, the needle protection. The co-operation between the elements and the counter elements, initiated by the needle protection moving in the proximal direction, guides the lock out of its resting position into an intermediate position from which it then—when the needle protection moves back into its initial position—passes into a locking or blocking position, wherein in a first step, the lock or parts of the lock can be elastically deformed, for example bent or twisted. Equally, the lock or parts of the lock can be permanently moved out of their resting position. A combination of reversible and irreversible adjustment is also conceivable and results in a change in the position of the lock or of a part or parts of the lock. In this changed position, the lock is then "armed", i.e. from this intermediate position, it can only then be moved into the locking position. Shortly before the needle protection reaches its protective position, after the medicine has been dispensed, the elastically deformed parts can spring back into their original position again, while irreversibly deformed or adjusted parts assume their new, changed position. The lock then assumes a position in which it securely prevents the needle protection from proximally shifting again.

In some embodiments, all the parts of the needle protecting unit are made of the same material, which is advantageous for recycling and helps prevent expensive waste separation. While it may be preferred for the needle protecting unit to form a unitary component together with the needle holder and the injection needle, the possibility is not be excluded that the needle protecting unit is a separate component which becomes a part of the injection device after it has been plugged on or attached to the device.

DETAILED DESCRIPTION

Figure 1:
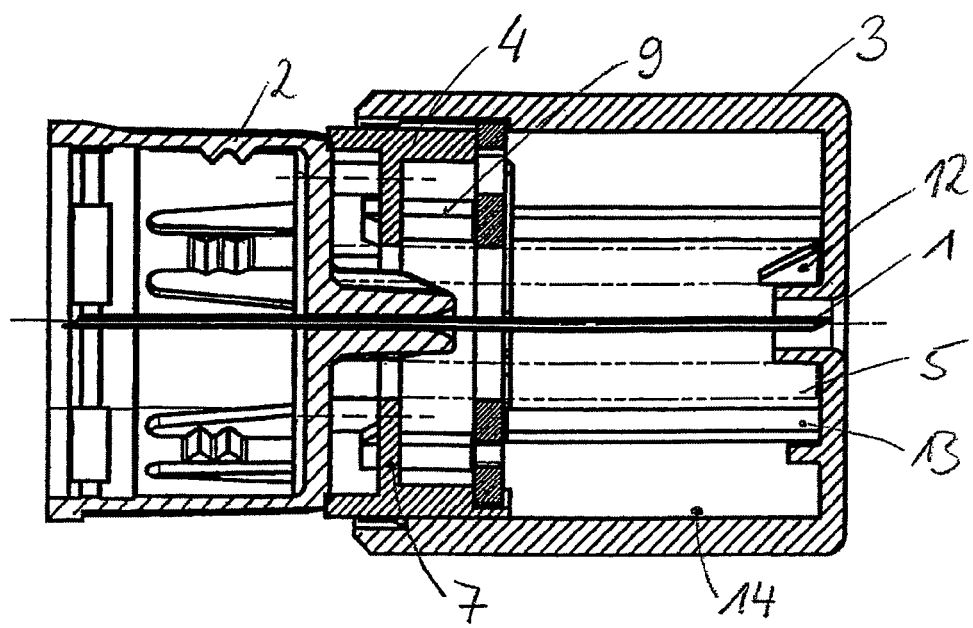
FIG. 1 depicts a needle unit of a first exemplary embodiment of the present invention, in cross-section, before a medicine is dispensed.

FIG. 1 shows a first embodiment of a needle unit in accordance with the invention. The needle unit comprises a needle support 2, out of which an injection needle 1 extends in the distal direction. The needle support 2 is formed such that its proximal side, i.e. its side pointing away from the needle tip intended for injecting into the skin, can be connected to an injection apparatus or ampoule. "Connected" includes both being screwed on by a thread and counter thread, being plugged, tensed or clamped on, or being connected by any other type of fastening which allows the needle holder to be held securely on the injection apparatus or ampoule. In the case of fastening on an ampoule or disposable injection apparatus, connections which cannot be non-destructively released are also included, while a releasable connection may be preferred in injection apparatus which are intended for multiple use.

A guiding part 4 is positioned on the needle support 2. This guiding part 4 is fixedly connected, for example glued or fused, to the needle support 2. It cannot therefore be moved in the axial direction relative to the needle support 2, nor can it be twisted on the needle support 2 or tilted to the side relative to the needle support 2. The guiding part 4 can, however, also be detachably fastened on the needle support 2, for example by a screw and/or clamp connection, as long as it is ensured that movement relative to the needle support 2 is securely ruled out during use. The guiding part 4 is a substantially annular body with an outer diameter which substantially corresponds to the outer diameter of the needle support 2. The guiding part 4 is arranged co-axially with respect to the injection needle 1 and the needle support 2. The guiding part 4 comprises a molded disc 7 which projects perpendicularly from the inner wall of the guiding part 4 and extends in the direction of the rotational axis. Slit-shaped openings 8 are introduced into said disc 7. At its distal end, the guiding part 4 is formed as a centering ring 11. The form and function of the centering ring 11 can be seen clearly in FIGS. 3a to 3c and are described in detail below in connection with these figures.

A tensing wheel 10 is connected, such that it cannot move axially but can rotate, to the guiding part 4 via connecting elements 9 which comprise hooks at their proximal end. The tensing wheel 10 is substantially a disc with recurrent recesses in the circumferential direction. Perpendicularly projecting connecting elements 9 are attached or molded to one of the flat sides of the tensing wheel 10. These connecting elements 9 comprise hook-shaped swellings at their end pointing away from the tensing wheel 10, via which they can hook in the slits 8 of the guiding part 4. To this end, the tensing wheel 10 is inserted into the guiding part 4 from above, i.e. from the distal side facing the needle tip, wherein the connecting elements 9 enter into engagement with the slits 8, and the lower end of the disc-shaped tensing wheel 10 abuts a collar formed in the guiding part 4 at the boundary with the centering ring 11. Since the connecting elements 9 are shaped such that they can only be moved through the slits 8 in one direction and are prevented from moving in the opposite direction, and since the underside of the disc-shaped body of the tensing wheel 10 lies fixedly on the collar formed on the guiding part 4, the tensing wheel 10 can then no longer be moved axially with respect to the guiding part 4. The slits 8 exhibit a length which is greater than the width of the connecting elements 9, hence the connecting elements 9 can move laterally, i.e. in the circumferential direction, in the slits 8. The tensing wheel 10 can thus be twisted in the slits relative to the guiding part 4 by at most a circular segment corresponding to the length of the slits 8.

The needle unit additionally comprises a needle protecting cover 3 which surrounds the injection needle 1 over its entire length both before and after the medicine is dispensed. This ensures that neither the patient—in the case of self-medication—nor the medical staff can injure themselves on the needle tip. The needle protecting cover 3 is substantially a hollow cylinder body which is open on one of its flat sides and almost closed on the opposite side. The outer side of the needle protecting cover 3 is regular, and the edges are chamfered at both ends of the hollow cylinder body.

On the almost closed side, the needle protecting cover 3 comprises a central opening through which the injection needle 1 is guided out of the needle protecting cover 3 to dispense the medicine. To establish the injection needle guiding function, the inside of the needle protecting cover 3 comprises a sleeve which projects in the proximal direction from the inner side of the distal end of the needle protecting cover 3 and encircles the central opening. Switching ramps 12 are likewise attached or molded to the inner side of the largely closed side of the needle protecting cover 3 and likewise project from it in the proximal direction. The function of these switching ramps 12 is to switch the lock from its resting position to its blocking position. This is also described in detail further below, in the discussion of FIGS. 3a to 3c. In the interior of the needle protecting cover 3, guiding ribs 13, 14 are also formed on the radial outer side, wherein the guiding ribs 14 are longer than the guiding ribs 13. The longer guiding ribs 14 extend substantially over the entire inner length of the needle protecting cover 3, while the shorter ribs 13 extend from the distal inner end of the needle protecting cover 3 to about level with the distal flat side of the tensing wheel. These shorter guiding ribs 13 are part of the lock 6, as shall also become clear further below.

Figure 2:
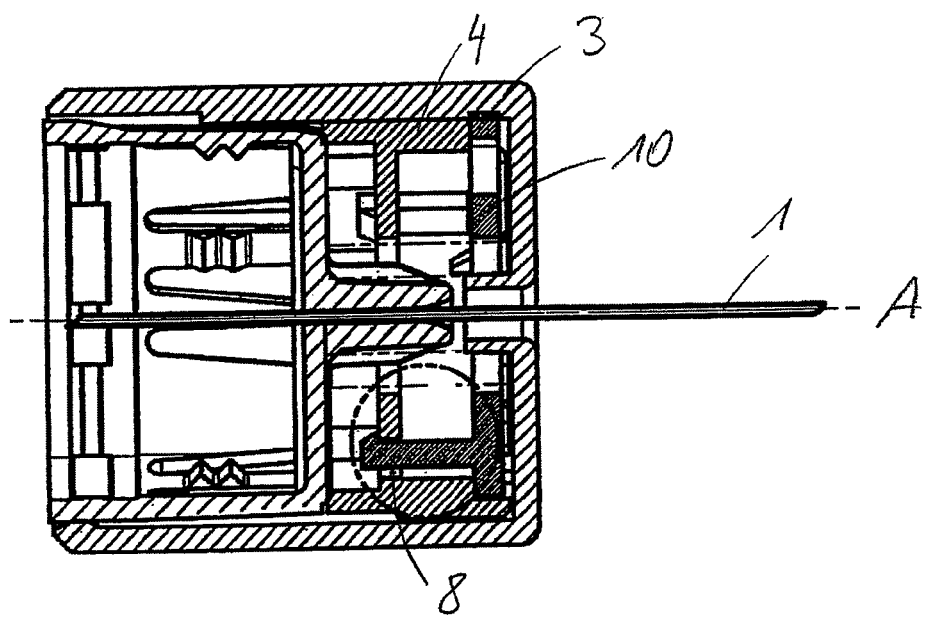
FIG. 2 shows the needle unit of FIG. 1, in cross-section, in which the needle protection has been fully slid or moved in the proximal direction and the lock is coupled to the needle protection.

FIG. 2 shows the needle protecting cover 3 in the position which it assumes when the medicine is dispensed. To this end, the distal end of the injection apparatus or syringe is placed onto the patient's skin. If pressure is then exerted on the syringe in the direction of the skin, the needle protecting cover 3 is shifted, against the force of a spring element 5, out of its resting position, in which it completely covers the injection needle 1, in the proximal direction. The injection needle 1 simultaneously emerges through the opening at the distal end of the needle protecting cover 3 and can be injected into the patient's skin. During this movement, the needle protecting cover 3 is guided on the guiding part 4, thus ensuring a largely linear movement of the needle protecting cover 3, i.e. without the needle protecting cover 3 laterally tilting away while the medicine is being dispensed. The needle protecting cover 3 continues to be moved in the proximal direction until the distal inner side of the needle protecting cover 3 is positioned on the guiding part 4. Special stopping elements can also be molded to the guiding part 4 or in the interior of the needle protecting cover 3 to limit the movement of the needle protecting cover 3 in the proximal direction. Elements or structure can also be provided on the ampoule body or injection device which limit the movement of the needle protecting cover 3 in the proximal direction when the medicine is dispensed.

Figure 3A:
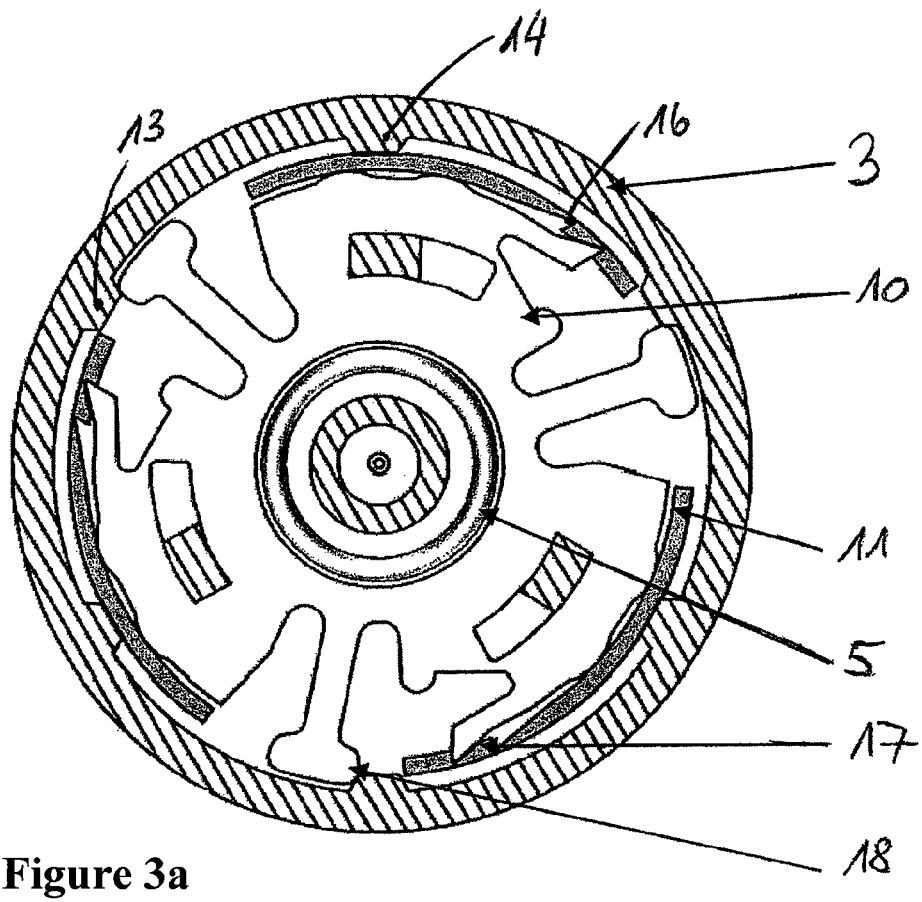
FIG. 3a is an enlarged view of the lock of the first exemplary embodiment, in its initial position.

Toward the end of the movement of the needle protecting cover 3 in the proximal direction, the switching ramps 12 enter into engagement with the tensing wheel 10. FIG. 3a shows the initial position of the tensing wheel 10 when installed in the guiding part 4, more specifically in the centering ring 11 formed on the guiding part 4. The centering ring 11 is sub-divided into three identical parts, wherein each of the three parts comprises two latching elements 15, 16 in the form of serrated recesses on its inner side. The tensing wheel 10 likewise comprises three identical partial regions, wherein each of the partial regions comprises a protrusion 17 which points radially outwards and forms the counter latching element to the latching elements 15, 16. The latching elements 15, 16 and the protrusion 17 are shaped such that the protrusion 17 can be moved out of the latching elements 15, 16 in one direction, while movement in the opposite direction is securely prevented. Each partial region of the tensing wheel 10 also comprises a trowel-shaped blocking element 18 which lies between two guiding ribs 13, 14 molded on the inside of the needle protecting cover 3 when the needle protecting cover 3 is in its resting state. The tensing wheel comprises recesses in the region of the blocking element 18 and the protrusion 17 which enable these two elements to be elastically deformed in the circumferential or radial direction. Each of the partial regions of the tensing wheel 10 comprises two hump-shaped moldings 19 on its radially outward side, which ensure that the tensing wheel 10 is centred in the centering ring 11 but simultaneously also that the friction forces which have to be overcome when rotating the tensing wheel 10 in the centering ring 11 are relatively small. FIG. 3a also clearly shows the spring element 5 which holds the needle protecting cover 3 in the distal position or guides it back to the distal position. The tensing wheel 10 also comprises recesses 20 shaped as bent elongated holes, with which the switching ramps 12 can engage.

Figure 3B:
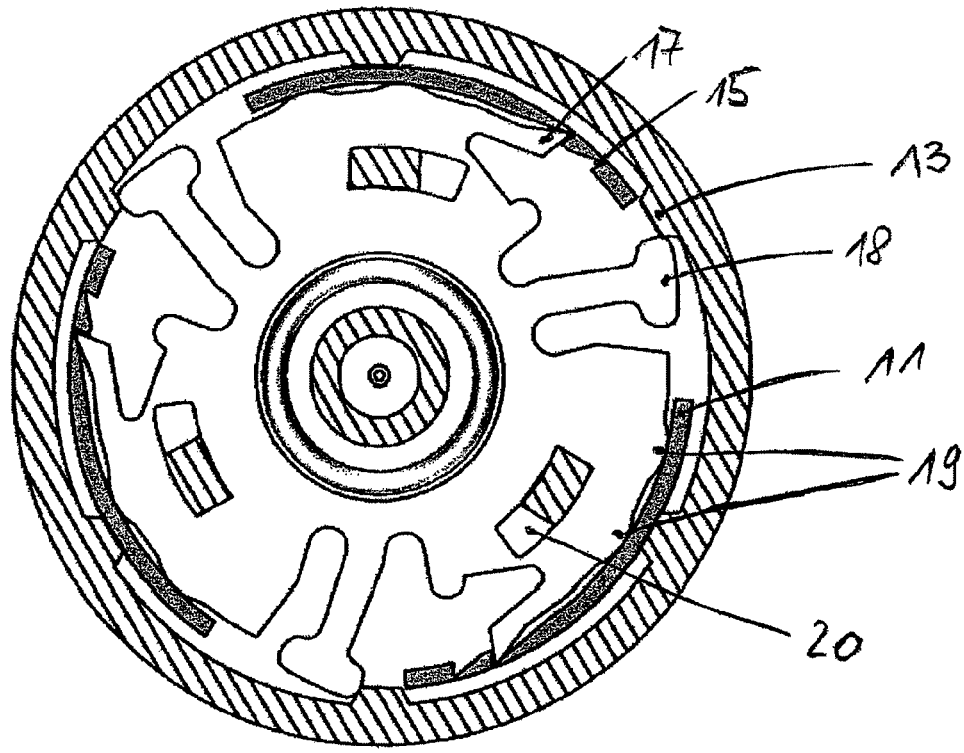
FIG. 3b is similar to FIG. 3a, but with the needle protection in its pressed position.
Figure 3C:
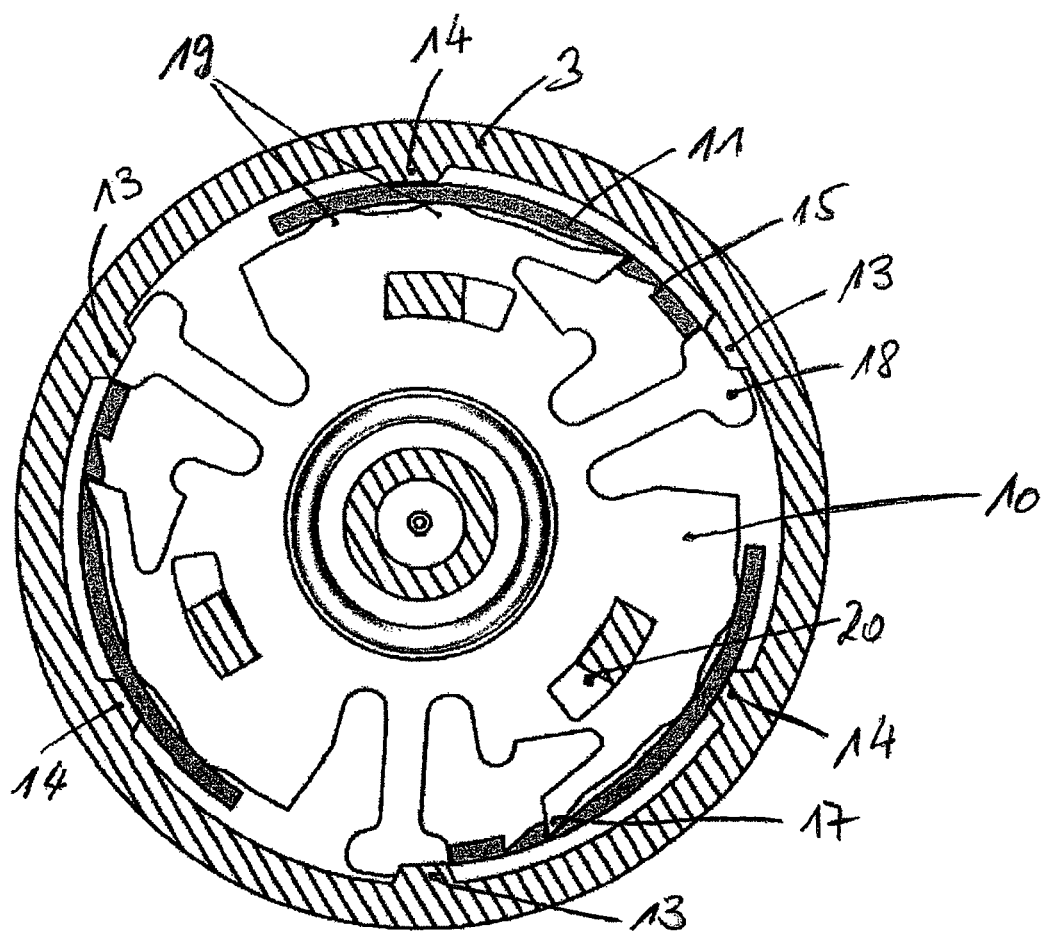
FIG. 3c is similar to FIG. 3a, but in its final position, i.e. the locked or locking position.

FIG. 3b shows the tensing wheel 10 and the centering ring 11 in the position which they assume when the needle protecting cover 3 is situated in its most proximal position. The switching ramps 12 (not shown) are in engagement with the recesses 20 on the tensing wheel. Due to their shape and arrangement in the needle protecting cover 3, the switching ramps 12 have, in the example, twisted the tensing wheel anti-clockwise, wherein the protrusion 17 has been shifted from the first latching element 15 to the second latching element 16, thus preventing the tensing wheel 10 from being rotated back. During the movement of the needle protecting cover 3 in the proximal direction, one of the shorter guiding ribs 13—which in its initial position lies next to the blocking element 18 in the circumferential direction, for example on the side in the anti-clockwise direction—is guided downwardly with it. This guiding rib 13 prevents the blocking element 18 from being able to be slaved in the forced rotational movement of the tensing wheel 10. Instead, the blocking element is pressed against the guiding rib 13 and elastically deformed counter to the rotational direction of the tensing wheel 10. Once the medicine has been completely dispensed, the injection needle is drawn out of the patient's skin, the pressure acting on the spring element 5 is released and the spring element 5 guides the needle protecting cover 3 back to its resting position, wherein the guiding rib 13 slides along the blocking element 18. Since the guiding rib 13 is a short guiding rib and, as already described further above, only extends over a partial length of the inner wall of the needle protecting cover 3, the elastically deformed blocking element 18 can snap back into its original position on the tensing wheel as soon as the guiding rib 13 terminates. As shown in FIG. 3c, the blocking element 18 then lies in the region of the short guiding rib 13, more specifically just below the guiding rib 13, which means the needle protecting cover 3 can no longer be shifted in the proximal direction.

The functionality of the lock 6, which in this example comprises the blocking or locking elements 18 and the short guiding ribs 13, has been described on the basis of FIGS. 3a to 3c. It should be understood that purpose, function and/or operation of the embodiment of the present invention just described may also be achieved using parts or components which are shaped or arranged differently. This shall be illustrated by the following second exemplary embodiment.

Figure 4:
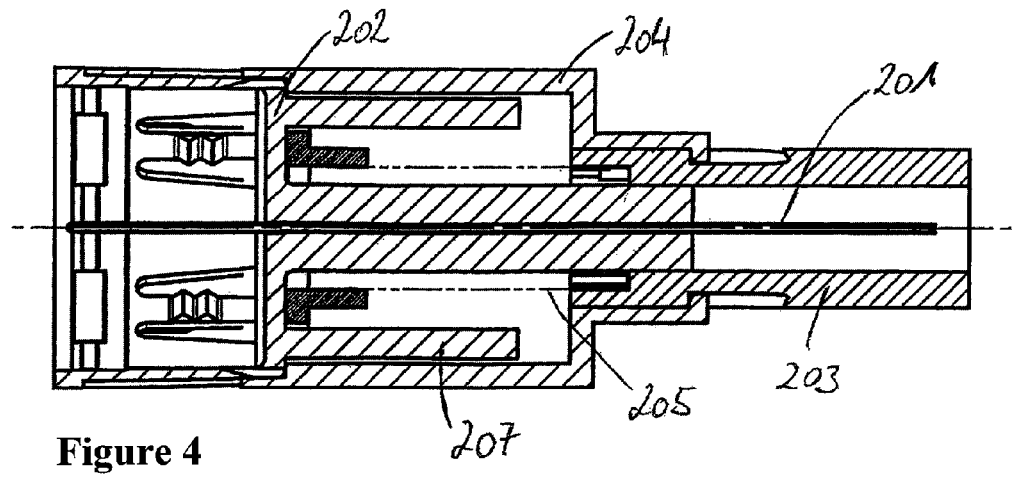
FIG. 4 shows a needle unit of a second exemplary embodiment of the present invention, in cross-section, before a medicine is dispensed.

A needle unit of a second embodiment in accordance with the present invention is shown in FIGS. 4 to 8. FIG. 4 shows the needle unit in its resting position, i.e. before use. The needle unit comprises a needle holder 202 which can be connected to an ampoule or injection device. The needle holder 202 comprises a centrally arranged sleeve 214 which extends in the distal direction and in which the injection needle is guided, and two blocking or locking elements 207 which likewise project from the needle holder 202 in the distal direction. The two blocking elements 207 lie opposite each other in relation to the longitudinal axis of the needle unit, i.e. the rotational axes of the sleeve 214 and the blocking elements 207 lie in one plane. The blocking elements 207—in the example, elastic round rods—are shorter than the sleeve 214, i.e. they do not protrude as far from the needle holder 202 in the distal direction. Instead of the round rods, other shapes—for example rectangular or hollow rods—can also be molded or fastened to the needle holder 202.

A disc-shaped element 215 is positioned on the needle holder 202, and hooks 208 pointing in the distal direction are molded on its flat distal side. The element 215 is substantially circular, with a central opening through which the sleeve 214 protrudes and two lateral, substantially semicircular recesses 209 which form a passage for the blocking elements 207 (see also in this respect FIGS. 7 and 8).

A guiding part 204 is also positioned on top of or on the side of the needle holder 202 and is connected to the needle holder 202 such that it cannot move axially and is secured against twisting or tilting. The guiding part 204 is a cylindrical body comprising, in the longitudinal direction, two sections having different diameters. The proximal part exhibits an inner diameter which is only slightly smaller than the outer diameter of the needle holder 202. The distal part of the guiding part 204 has a smaller diameter than the proximal part, and two protrusions 211 pointing radially inwards are molded to its most proximal end.

A needle protecting cover 203 is part of the needle unit. The needle protecting cover 203 consists—as can be gathered particularly clearly from FIG. 8—substantially of a cylindrical body comprising coupling elements 212 molded or formed on its proximal side, to which hooks 208 of the element 215 can be coupled. Wedged rails 210 are formed on the cylindrical part of the needle protecting cover and can co-operate with the protrusions 211 of the guiding part 204, thus twisting the needle protecting cover 203 relative to the guiding part 204 when it is moved in the proximal direction.

Figure 5:
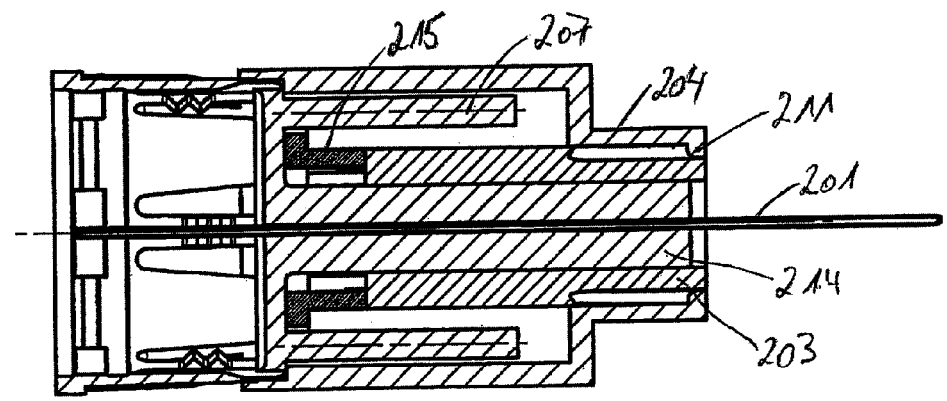
FIG. 5 depicts the needle unit of FIG. 4, in cross-section, in which the needle tip protection has been fully slid or moved in the proximal direction and the lock is coupled to the needle protection.
Figure 6:
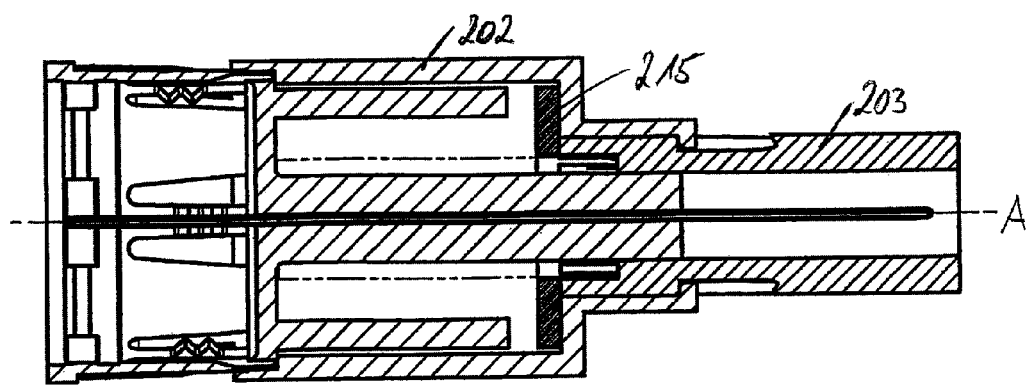
FIG. 6 shows the needle unit of FIG. 4, in cross-section, after the medicine has been dispensed, with the lock in the blocking position.
Figure 7:
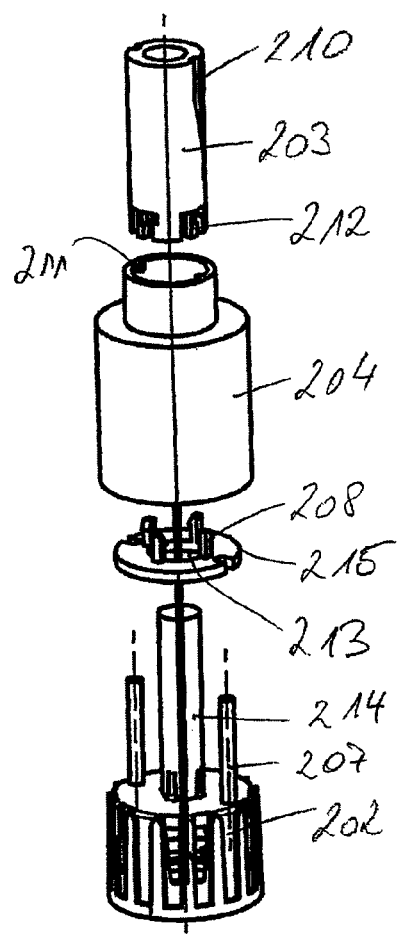
FIG. 7 is an exploded drawing of the needle unit of FIG. 4.
Figure 8:
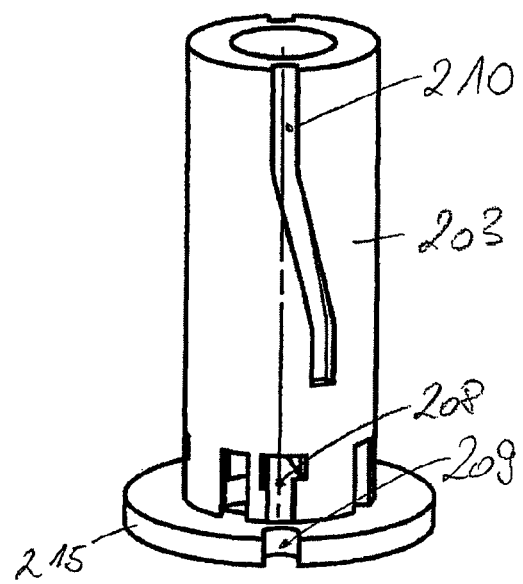
FIG. 8 shows an embodiment of a needle protecting cover of the needle unit of FIG. 4.

FIG. 5 shows the situation in which the needle protecting cover 203 is completely slid or moved back. The needle protecting cover 203 is slid back by placing the distal end of the needle unit onto the patient's skin and exerting pressure onto the injection apparatus or ampoule in the direction of the skin. The needle protecting cover 203 is shifted in the proximal direction, against the restoring force of a spring element 205. When the needle protecting cover 203 is slid back in the proximal direction, the needle protecting cover 203 is firstly linearly guided in the direction of the needle holder 202 in accordance with the shape of the wedged rails 210, then twisted by a predetermined angle and lastly guided linearly again. In the final section of the movement, the coupling elements 212 enter into coupling engagement with the hooks 208 and establish a secure and non-releasable connection between the needle protecting cover 203 and the element 215, Once the medicine has been completely dispensed, the injection needle 201 is drawn out of the patient's skin, and the spring element 205 presses the needle protecting cover 203 back into its resting and/or needle covering position. During this movement, the needle protecting cover 203 slaves the coupled element 215. Due to the shape of the wedged rails 210, the first part of the movement runs linearly, thus lifting the element 215 and guiding it some way in the distal direction. When the part of the wedged rails 210 is reached which causes the needle protecting cover 203 to be twisted relative to the guiding part 204, the blocking elements 207 guided in the recesses 209 are elastically deformed, for example bent. When or shortly before the resting position is reached, the recesses 209 of the element 215 release the blocking elements 207 from their guidance. The elastically deformed blocking elements 207 are able to spring back into their initial position and, due to the twisting of the element 215, then come to rest in a region below the element 215 which does not comprise any recesses 209. This securely prevents the needle protecting cover 203 from being shifted again in the proximal direction. The element 215 and the blocking elements 207 together form the lock 206.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle unit for an injection device having an injection needle and a needle holder, the needle unit comprising:
   a guiding part securable to the needle holder;
   a cover longitudinally slidable along the guiding part, the cover comprising a longitudinally extending guiding rib on an inner surface thereof and a switching ramp extending in a proximal direction from the cover; and
   a substantially planar tensing wheel longitudinally slaved to the guiding part, the tensing wheel comprising:
      a recess extending through the wheel and adapted to receive the switching ramp thereby causing rotational motion of the tensing wheel; and
      a radially extending blocking element adapted to interface with the guiding rib, wherein:
   proximal motion of the cover relative to the injection device causes rotation of the tensing wheel via interaction between the switching ramp and the recess, the rotation causing the blocking element to flexibly engage the guiding rib; and
   subsequent distal motion of the cover causes a proximal end of the guiding rib to clear the blocking element allowing the blocking element to release to a position generally in line with the guiding rib thereby preventing additional proximal motion of the cover.

2. The needle unit of claim 1, wherein:
   the guiding part further comprises a centering ring having a plurality of latching elements on an inner surface thereof; and
   the tensing wheel further comprises a generally circumferentially extending flexible protrusion adapted to engage at least one of the plurality of latching elements, wherein rotation of the tensing wheel causes the protrusion to move between latching elements of the plurality of latching elements.

3. The needle unit of claim 2, wherein the tensing wheel further comprises moldings adapted to maintain the tensing wheel centered in the centering ring.

4. The needle unit of claim 1, wherein:
   the tensing wheel includes connecting elements extending therefrom to the guiding part; and
   the guiding part comprises a disc including slits adapted to receive the connecting elements.

5. The needle unit of claim 1, further comprising a biasing mechanism adapted to bias the cover in a distal direction.

6. The needle unit of claim 5, wherein the blocking elements are trowel-shaped.

7. The needle unit according to claim 2, wherein the guiding part includes a centering ring at a distal end of the guiding part, the latching elements being positioned on an inner surface thereof.

8. The needle unit according to claim 2, wherein the latching elements, in co-operation with the protrusions, allow the tensing wheel to be twisted in one direction but securely prevent the tensing wheel from being twisted in the opposite direction.

9. The needle unit according to claim 2, wherein the tensing wheel radially and circumferentially comprises a number of identical arrays, each array comprising a blocking element, a protrusion, and a cut out there between.

10. The needle unit according to claim 1, wherein the longitudinally extending guiding rib comprises a plurality of longitudinally extending short guiding ribs, the guiding part further comprising a plurality of longitudinally extending long guiding ribs staggered with the short ribs, and wherein, when the needle unit is in a resting state, the blocking elements lie between the short guiding ribs and long guiding ribs, and when the tensing wheel is rotated, the blocking elements are prevented from rotating with it by the short guiding ribs and are elastically biased counter to the direction of the rotation.

11. A needle unit for an injection device having an injection needle and a needle holder, the needle unit comprising:
   a guiding part rigidly securable to the needle holder to prevent relative movement there between, the guiding part comprising a disc at a proximal end and a centering ring at a distal end, the disc having slits passing there through, the centering ring comprising a plurality of sub-divided ring portions separated by a gap, each of the sub-divided ring portions having latching elements positioned on an inner surface thereof;
   a cover sleevably positioned over and longitudinally slidable along the guiding part, the cover comprising a plurality of longitudinally extending guiding ribs on an inner surface thereof and a plurality of switching ramps extending in a proximal direction from the cover; and
   a substantially planar tensing wheel longitudinally slaved to the guiding part, the tensing wheel comprising:
      connecting elements extending from the tensing wheel and engaged in the slits of the guiding part, the slits extending in a circumferential direction and having a circumferential length greater than a width of the connecting elements to allow relative rotation between the tensing wheel and the guiding part;
      a plurality of recesses extending through the wheel, each recess adapted to receive a switching ramp of the plurality of switching ramps to collectively cause rotational motion of the tensing wheel;

a plurality of protrusions adapted to engage one of the plurality of latching elements, the engagement providing for rotational motion of the tensing wheel relative to the guiding part in a single direction; and a plurality of radially extending blocking elements each adapted to interface with one of the plurality of guiding ribs, wherein:

proximal motion of the cover relative to the injection device causes rotation of the tensing wheel via interaction between the switching ramp and the recess, the rotation causing each of the plurality of protrusions to move to adjacent latching elements and each of the blocking elements to flexibly engage one of the plurality of guiding ribs; and subsequent distal motion of the cover causes a proximal end of the plurality of guiding ribs to clear the plurality of blocking elements allowing the blocking elements to release to a position generally in line with the plurality of guiding ribs thereby preventing additional proximal motion of the cover.

* * * * *